(12) United States Patent
Gomez

(10) Patent No.: US 6,520,940 B1
(45) Date of Patent: Feb. 18, 2003

(54) PATIENT MOUNTED I/V PROTECTOR APPARATUS

(76) Inventor: Roy C. Gomez, 537 Linwood Dr., Richlands, VA (US) 24641

( * ) Notice: Subject to any disclaimer, the term of this patent is extended or adjusted under 35 U.S.C. 154(b) by 0 days.

(21) Appl. No.: 09/862,638

(22) Filed: May 22, 2001

(51) Int. Cl.[7] ................................................. A61M 5/32
(52) U.S. Cl. ........................ 604/179; 602/21; 128/879; 128/DIG. 6
(58) Field of Search ................................ 604/174, 179; 602/5, 12, 21; 128/877, 878, 879, DIG. 6

(56) References Cited

U.S. PATENT DOCUMENTS

| | | | | |
|---|---|---|---|---|
| 5,018,534 A | * | 5/1991 | Grant | 128/877 |
| 5,279,574 A | * | 1/1994 | Forren | 128/879 |
| 5,339,834 A | * | 8/1994 | Marcelli | 128/877 |
| 5,413,120 A | * | 5/1995 | Grant | 128/877 |
| 5,682,905 A | * | 11/1997 | Grant | 128/877 |
| 5,785,057 A | * | 7/1998 | Fischer | 128/846 |
| 5,827,207 A | * | 10/1998 | MacMorran | 128/845 |
| 5,925,007 A | * | 7/1999 | Ashline | 128/878 |
| 6,042,568 A | * | 3/2000 | Gomez | 128/DIG. 6 |

* cited by examiner

Primary Examiner—Michael J. Hayes
Assistant Examiner—Mark Han
(74) Attorney, Agent, or Firm—Steptoe & Johnson PLLC

(57) ABSTRACT

A patient mounted I/V protector apparatus includes a first limb reception portion having locking finger reception channels which is placed under a patient's arm A second limb reception portion is connected to the first limb reception portion. The second limb reception portion includes locking fingers having barbed finger ends which are placed in registration with the locking finger reception channels for locking the second limb reception portion to the first limb reception portion. The locking finger reception channels include barb engagement ledges for engaging the barbed finger ends. One or more unlocking keys are provided, for releasing the locking fingers from the barb engagement ledges, to release the second limb reception portion from the first limb reception portion.

13 Claims, 4 Drawing Sheets

PATIENT MOUNTED I/V PROTECTOR APPARATUS

BACKGROUND OF THE INVENTION

1. Field of the Invention

The present invention relates generally to intravenous (I/V) administration apparatus, and, more particularly, to I/V apparatus especially adapted for retaining an I/V needle in a desired position on a patient's extremity.

2. Description of the Prior Art

When an I/V needle is in a patient's extremity, such as a patient's arm, it is important that the I/V needle not be moved or dislodged from its intravenous position in the patient. Patients who are children often have a special propensity for disturbing an I/V needle from its desired intravenous position. In this respect, it would be desirable if a device were provided that can be used with young patients to retain an I/V needle in a desired intravenous position.

Presently, to retain an I/V needle in a desired intravenous position in a patient's forearm, a hard board splint is placed under the forearm, and a portion of the I/V apparatus, the patient's forearm, and the splint are taped together. Yet, even with this splint technique, the portion of the I/V needle that is outside the patient's arm can be touched or disturbed by the patient. In this respect, it would be desirable if a device were provided that covers the portion of the I/V needle that is outside the patient's arm so as to prevent the patient from touching or disturbing the I/V needle.

Another difficulty that may arise from using the splint technique just described is related to the accessibility to the patient of the portion of the I/V line that is near the I/V needle. If the portion of the I/V line that is near the I/V needle is pulled, such pulling may disturb the portion of the I/V needle that is in the patient. In this respect, it would be desirable if a device were provided that protects the portion of the I/V line that is adjacent to the I/V needle from being pulled by the patient.

Even if the portion of the I/V line adjacent to the I/V needle is protected from interference by the patient, there is the possibility that if the I/V line is pulled on a significant distance away from the I/V needle, the pulling force can be transmitted through the I/V line to the I/V needle. To prevent such forces on the I/V line from being transmitted along the I/V line to the I/V needle, it would be desirable if a device were provided that blocks a distal pulling force on an I/V line from being transmitted through the I/V line to the I/V needle.

Still other features would be desirable in a patient mounted I/V protector apparatus. For example, it would be desirable if an I/V protector apparatus could be easily fixed to an removed from a patient's forearm. It would also be desirable if an I/V protector apparatus were ornamented with attractive decorations, such as cartoon characters, which are appealing to children. Also, it would be desirable if an I/V protector apparatus could be written upon to receive personalized messages or signatures of friends and loved ones.

It is noted that the present inventor has patented U.S. Pat. No. 6,042,568, incorporated herein by reference. The patient mounted I/V protector apparatus disclosed in U.S. Pat. No. 6,042,568 provides for straps and well known VELCRO(™) material located on the outside of limb reception portions. Being on the outside of the limb reception portions, the straps and VELCRO(™) material can be tampered with by children's hands. As a result, a persistent child may be able to disconnect the straps and remove the top limb reception portion from the bottom limb reception portion to expose the I/V connection to the child. In this respect, it would be desirable if a patient mounted I/V protector apparatus were provided which precludes a child from disconnecting a top limb reception portion from a bottom limb reception portion.

To further improve the security of the patient mounted I/V protector apparatus, it would be desirable if when the top limb reception portion is connected to the bottom limb reception portion in such a way that a key is needed to disconnect the top limb reception portion from the bottom limb reception portion.

For ease of fitting the top limb reception portion onto the bottom limb reception portion, it would be desirable if the top limb reception portion were connected to the bottom limb reception portion, in part, by a hinge or pivoting motion.

For ease of securing the top limb reception portion to the bottom limb reception portion, it would be desirable if the top limb reception portion has a snap lock connection to the bottom limb reception portion.

Thus, while the foregoing indicates it to be well known to use a splint to protect an I/V needle in a patient, the foregoing does not teach or suggest a patient mounted I/V protector apparatus which has the following combination of desirable features: (1) can be used with young patients to retain an I/V needle in a desired intravenous position; (2) covers the portion of the I/V needle that is outside the patient's arm so as to prevent the patient from touching or disturbing the I/V needle; (3) protects the portion of the I/V line that is adjacent to the I/V needle from being pulled by the patient; (4) blocks a distal pulling force on an I/V line from being transmitted through the I/V line to the I/V needle; (5) can be easily fixed to an removed from a patient's forearm; (6) can be ornamented with attractive decorations, such as cartoon characters, which are appealing to children; (7) can be written upon to receive personalized messages or signatures of friends and loved ones; (8) precludes a child from disconnecting a top limb reception portion from a bottom limb reception portion; (9) needs a key to disconnect the top limb reception portion from the bottom limb reception portion; (10) provides that the top limb reception portion is connected to the bottom limb reception portion, in part, by a hinge or pivoting motion; and (11) provides a snap lock connection between the top limb reception portion and the bottom limb reception portion. The foregoing desired characteristics are provided by the unique patient mounted I/V protector apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides a patient mounted I/V protector apparatus which includes first limb reception portion which is placed under a patient's arm. The first limb reception portion includes locking finger reception channels. A second limb reception portion is connected to the first limb reception portion. The second limb reception portion includes locking fingers which are placed in registration with the locking finger reception channels for locking the second limb reception portion to the first limb reception portion. When the first limb reception portion and the second limb reception portion are connected together on a patient's arm, an I/V needle and tubing connected to the patient's arm is prevented from being disturbed by the patient.

The first limb reception portion includes straps for securing the patient's arm to the first limb reception portion. Each of the straps includes strap ends, wherein one of the strap ends includes a quantity of a hook-or-loop connector and another of the strap ends includes a quantity of complimentary loop-or-hook connector.

The locking fingers are flexible. The locking fingers include barbed finger ends. The locking finger reception channels include barb engagement ledges for engaging the barbed finger ends. The locking fingers are located on a front side of the second limb reception portion, and the locking finger reception channels and the barb engagement ledges are located on a front side of the first limb reception portion. Key reception channels are adjacent to the locking finger reception channels in the first limb reception portion. One or more unlocking keys are provided, each of which includes an unlocking end and a handle end. The unlocking ends are received in the key reception channels.

Guide pins project upward from a rear side of the first limb reception portion. Guide slots are located on a rear side of the second limb reception portion. The guide slots are registrable with the guide pins. Hinge pins are supported horizontally on the rear side of the first limb reception portion, and hinge-engagement members are supported on the rear side of the second limb reception portion. Each of the hinge-engagement members includes a hinge-pin-reception well for being placed in registration with and for receiving a hinge pin.

An I/V tubing support member projects upward from the first limb reception portion, and tubing securement members are attached to the I/V tubing support member. The I/V tubing support member includes a tubing reception channel. The second limb reception portion includes ventilation channels. An arm-reception cushion is supported on the first limb reception portion.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining a preferred embodiment of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved patient mounted I/V protector apparatus which has all of the advantages of the prior art and none of the disadvantages.

It is another object of the present invention to provide a new and improved patient mounted I/V protector apparatus which may be easily and efficiently manufactured and marketed.

It is a further object of the present invention to provide a new and improved patient mounted I/V protector apparatus which is of durable and reliable construction.

An even further object of the present invention is to provide a new and improved patient mounted I/V protector apparatus which is susceptible of a low cost of manufacture with regard to both materials and labor, and which accordingly is then susceptible of low prices of sale to the consuming public, thereby making such patient mounted I/V protector apparatus available to the buying public.

Still yet a further object of the present invention is to provide a new and improved patient mounted I/V protector apparatus which can be used with young patients to retain an I/V needle in a desired intravenous position.

Still another object of the present invention is to provide a new and improved patient mounted I/V protector apparatus that covers the portion of the I/V needle that is outside the patient's arm so as to prevent the patient from touching or disturbing the I/V needle.

Yet another object of the present invention is to provide a new and improved patient mounted I/V protector apparatus which protects the portion of the I/V line that is adjacent to the I/V needle from being pulled by the patient.

Even another object of the present invention is to provide a new and improved patient mounted I/V protector apparatus that blocks a distal pulling force on an I/V line from being transmitted through the I/V line to the I/V needle.

Still a further object of the present invention is to provide a new and improved patient mounted I/V protector apparatus which can be easily fixed to an removed from a patient's forearm.

Yet another object of the present invention is to provide a new and improved patient mounted I/V protector apparatus that can be ornamented with attractive decorations, such as cartoon characters, which are appealing to children.

Still another object of the present invention is to provide a new and improved patient mounted I/V protector apparatus which can be written upon to receive personalized messages or signatures of friends and loved ones.

Still yet a further object of the present invention is to provide a new and improved patient mounted I/V protector apparatus which precludes a child from disconnecting a top limb reception portion from a bottom limb reception portion.

Still another object of the present invention is to provide a new and improved patient mounted I/V protector apparatus that needs a key to disconnect the top limb reception portion from the bottom limb reception portion.

Yet another object of the present invention is to provide a new and improved patient mounted I/V protector apparatus which provides that the top limb reception portion is connected to the bottom limb reception portion, in part, by a hinge or pivoting motion.

Even another object of the present invention is to provide a new and improved patient mounted I/V protector apparatus that provides a snap lock connection between the top limb reception portion and the bottom limb reception portion.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein.

DESCRIPTION OF THE PREFERRED EMBODIMENT

Figure 1:
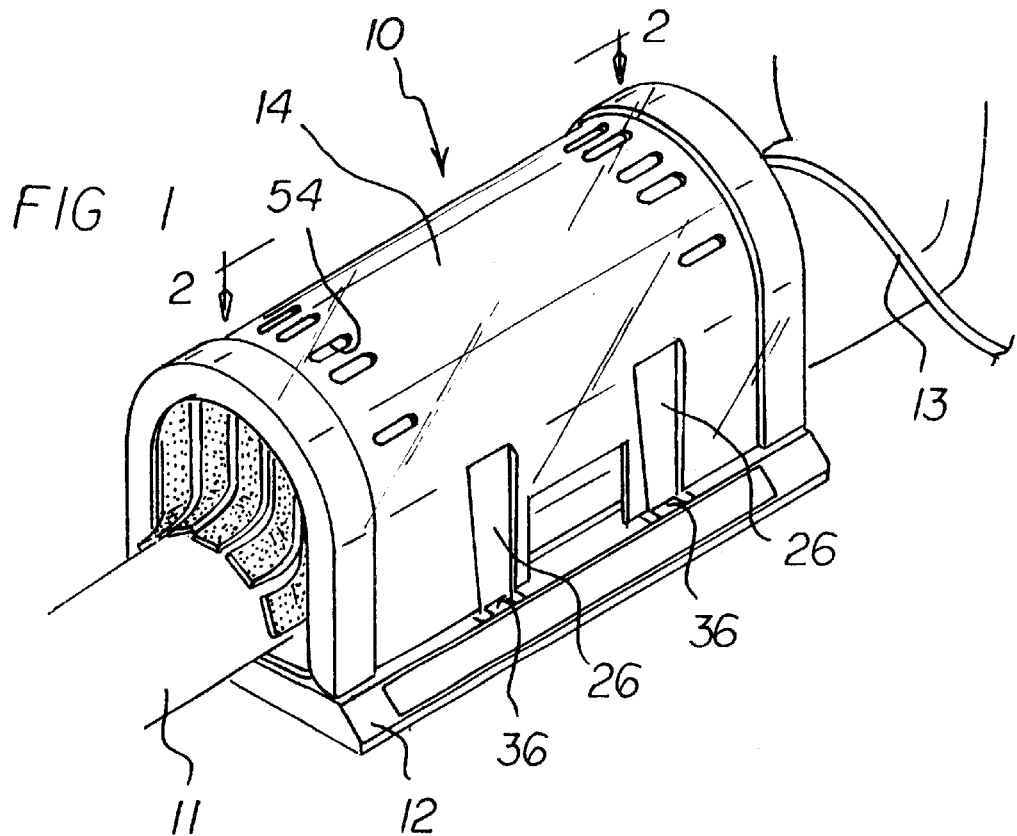
FIG. 1 is a perspective view showing a preferred embodiment of the patient mounted I/V protector apparatus of the invention.
Figure 2:
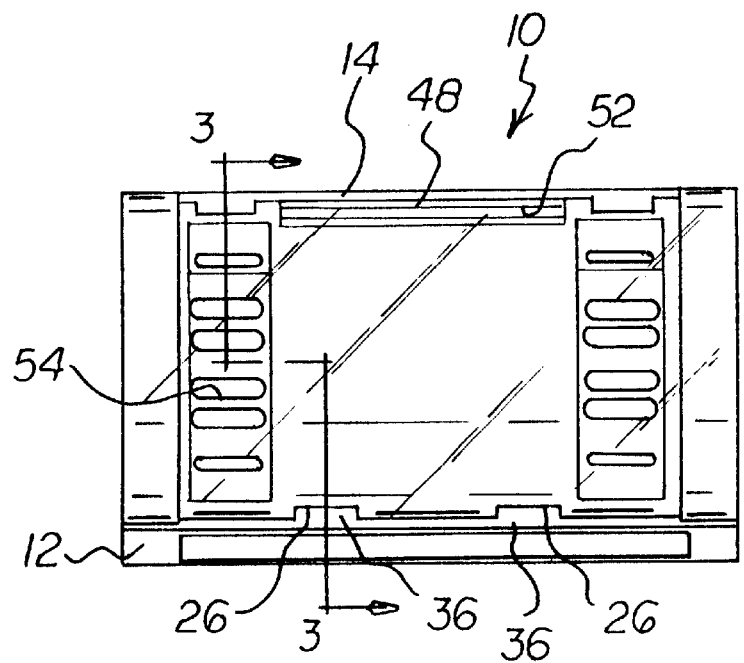
FIG. 2 is a top view of the embodiment of the patient mounted I/V protector apparatus shown in FIG. 1 taken along line 2—2 of FIG. 1.
Figure 3:
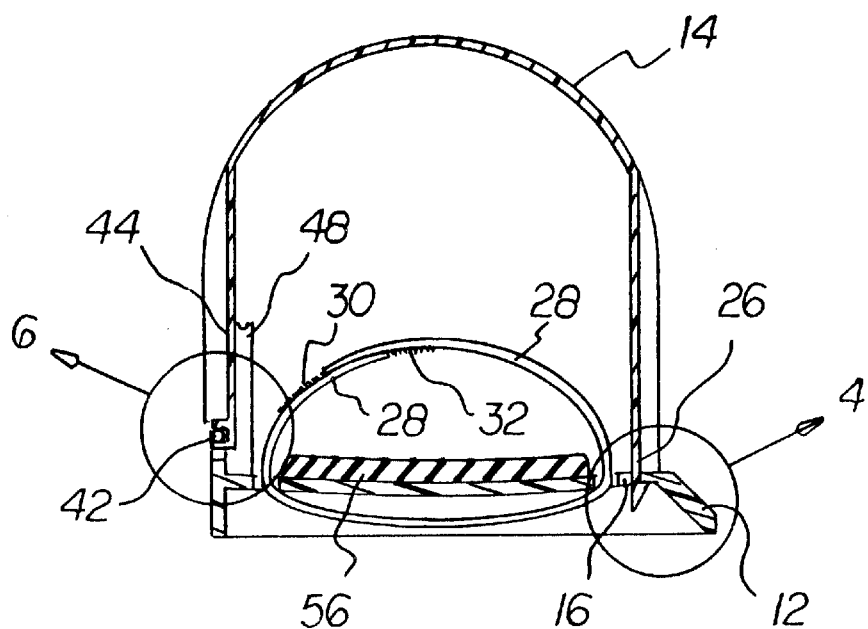
FIG. 3 is a cross-sectional view of the embodiment of the patient mounted I/V protector apparatus of FIG. 2 taken along line 3—3 thereof.

With reference to the drawings, a new and improved patient mounted I/V protector apparatus embodying the principles and concepts of the present invention will be described.

Turning to FIGS. 1–7, there is shown an exemplary embodiment of the patient mounted I/V protector apparatus of the invention generally designated by reference numeral 10. In its preferred form, patient mounted I/V protector apparatus 10 includes a first limb reception portion 12 which is placed under a patient's arm 11. The first limb reception portion 12 includes locking finger reception channels 16. A second limb reception portion 14 is connected to the first limb reception portion 12. The second limb reception portion 14 includes locking fingers 26 which are placed in registration with the locking finger reception channels 16 for locking the second limb reception portion 14 to the first limb reception portion 12.

The first limb reception portion 12 includes straps 28 for securing the patient's arm 11 to the first limb reception portion 12. Each of the straps 28 includes strap ends, wherein one of the strap ends includes a quantity of a hook-or-loop connector 30 and another of the strap ends includes a quantity of complimentary loop-or-hook connector 32.

The locking fingers 26 are flexible. The locking fingers 26 include barbed finger ends 34. The locking finger reception channels 16 include barb engagement ledges 36 for engaging the barbed finger ends 34. The locking fingers 26 are located on a front side of the second limb reception portion 14, and the locking finger reception channels 16 and the barb engagement ledges 36 are located on a front side of the first limb reception portion 12. Key reception channels 18 are adjacent to the locking finger reception channels 16 in the first limb reception portion 12. One or more unlocking keys 20 are provided, each of which includes an unlocking end 22 and a handle end 24. The unlocking ends 22 are received in the key reception channels 18.

Guide pins 38 project upward from a rear side of the first limb reception portion 12. Guide slots 40 are located on a rear side of the second limb reception portion 14. The guide slots 40 are registrable with the guide pins 38. Hinge pins 42 are supported horizontally on the rear side of the first limb reception portion 12, and hinge-engagement members 44 are supported on the rear side of the second limb reception portion 14. Each of the hinge-engagement members 44 includes a hinge-pin-reception well 46 for being placed in registration with and for receiving a hinge pin 42.

An I/V tubing support member 48 projects upward from the first limb reception portion 12, and tubing securement members 50 are attached to the I/V tubing support member 48. The tubing securement members 50 can take the form of strips of adhesive tape. The I/V tubing support member 48 includes a tubing reception channel 52. The second limb reception portion 14 includes ventilation channels 54. An arm-reception cushion 56 is supported on the first limb reception portion 12.

To use the patient mounted I/V protector apparatus 10 of the invention, a patient's arm 11 is placed on the arm-reception cushion 56 on the first limb reception portion 12. The patient's arm 11 has an I/V needle (not shown) inserted therein, and I/V tubing 13 runs from the needle to a solution bag (not shown). The patient's arm 11 arm is secured to the first limb reception portion 12 by using the straps 28 to encompass portions of the patient's arm 11. Then, the hook-or-loop connectors 30 and the complimentary loop-or-hook connectors 32 of the straps 28 are interconnected to secure the patient's arm 11 to the first limb reception portion 12. A portion of the I/V tubing 13 is placed in the tubing reception channel 52 in the I/V tubing support member 48, and the tubing securement members 50 are used to secure the I/V tubing 13 to the I/V tubing support member 48. The I/V tubing support member 48 and the tubing securement members 50 prevent push and pull forces on the I/V tubing 13 from being transmitted to the needle and the patient's arm 11.

Figure 6:
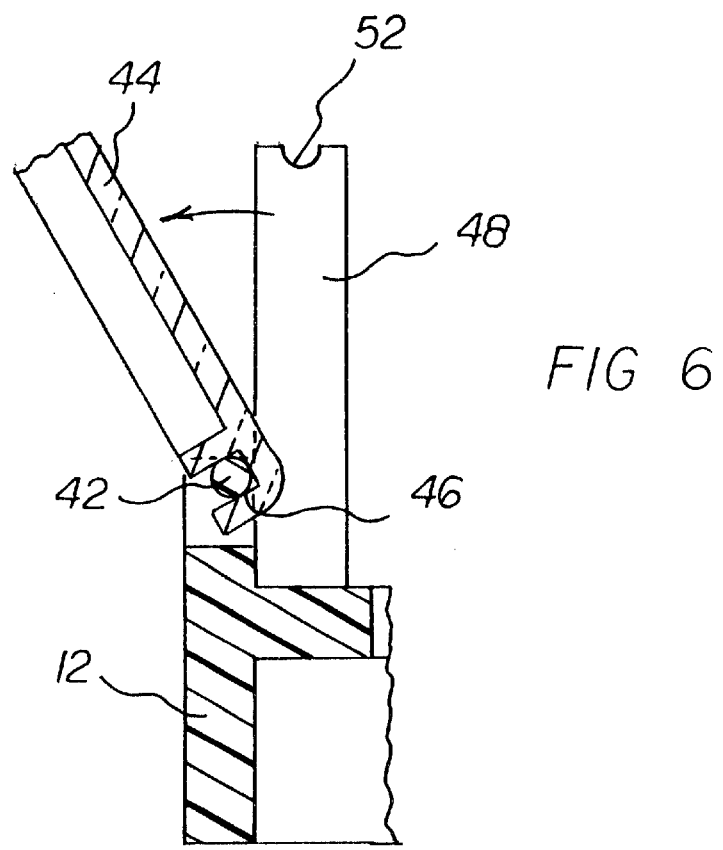
FIG. 6 is an enlarged view of the portion of the embodiment of the invention shown in FIG. 3 contained in circled region 6 thereof.
Figure 7:
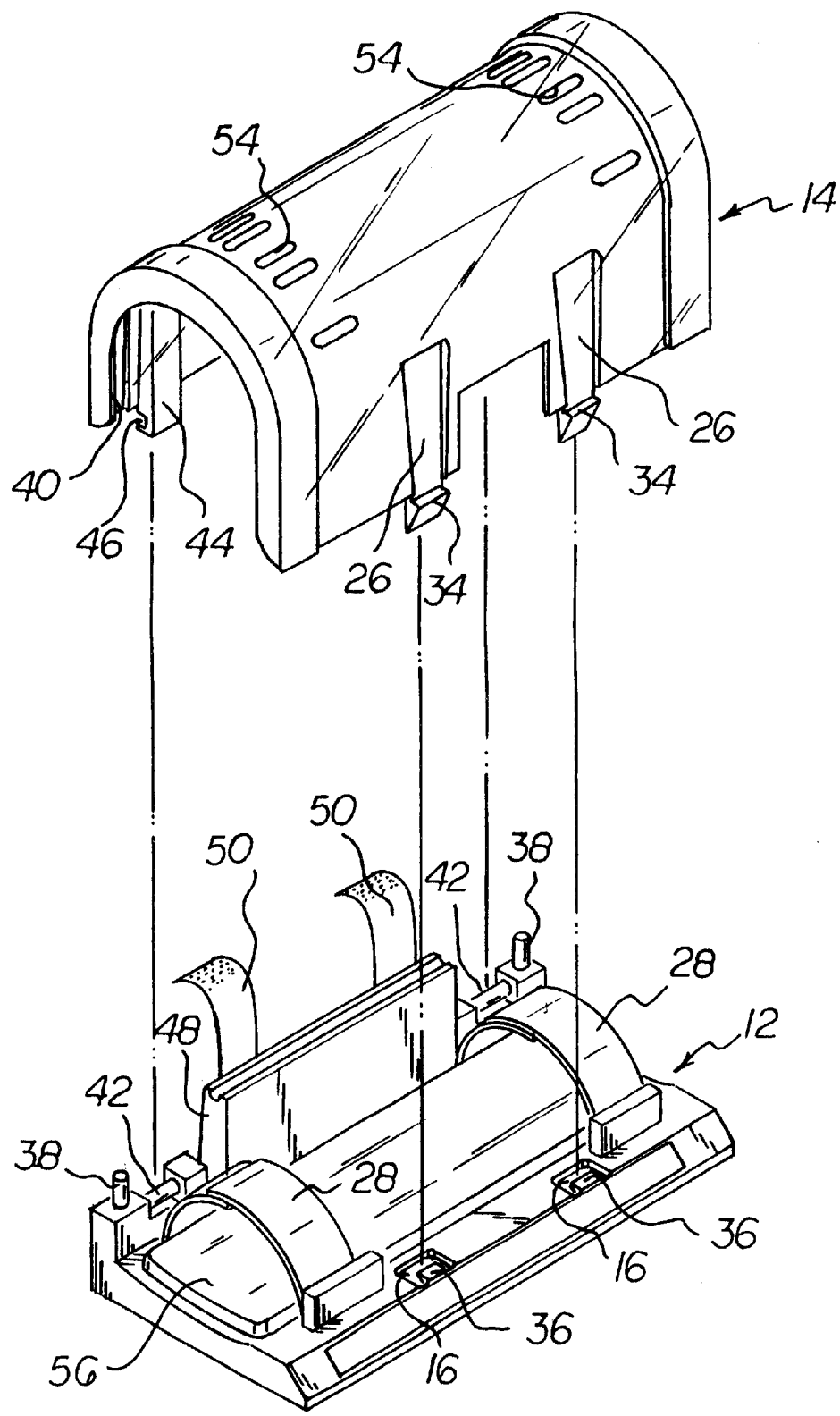
FIG. 7 is an exploded perspective view of the embodiment of the invention shown in FIGS. 1–6.

Once the patient's arm 11 is secured to the first limb reception portion 12, the second limb reception portion 14 is secured to the first limb reception portion 12 to cover and protect the patient's arm 11, the I/V tubing support member 48, and the I/V needle in the patient's arm 11. To do this, the second limb reception portion 14 is brought to the first limb reception portion 12 with the second limb reception portion 14 tilted backward, as shown in FIG. 6. The guide slots 40 are brought into registration with the guide pins 38, whereby the hinge-pin-reception wells 46 of the hinge-engagement members 44 are brought into engagement with the hinge pins 42 of the first limb reception portion 12. Once the guide pins 38 are in engagement with the guide slots 40 and the hinge-pin-reception wells 46 are in engagement with the hinge pins 42, the second limb reception portion 14 is tilted forward. As a result, the second limb reception portion 14 rotates around the hinge pins 42 so that the opposite side of the second limb reception portion 14 is lowered towards the side of the first limb reception portion 12 which is opposite to the guide pins 38.

When the second limb reception portion 14 is lowered sufficiently, the barbed finger ends 34 of the locking fingers 26 pass through the locking finger reception channels 16, and the second limb reception portion 14 is locked to the first limb reception portion 12 with the barbed finger ends 34 engaging the barb engagement ledges 36 of the first limb reception portion 12. Once the barbed finger ends 34 are in engagement with the barb engagement ledges 36, the second limb reception portion 14 cannot be lifted off of the first limb reception portion 12 until the barbed finger ends 34 are disengaged from the barb engagement ledges 36.

The barbed finger ends 34 are not readily disengaged from the barb engagement ledges 36 simply by using a person's unaided fingers. As a result, a child or other patient cannot readily disengage the second limb reception portion 14 from the first limb reception portion 12 and cannot readily disturb an I/V needle in the arm.

Figure 4:
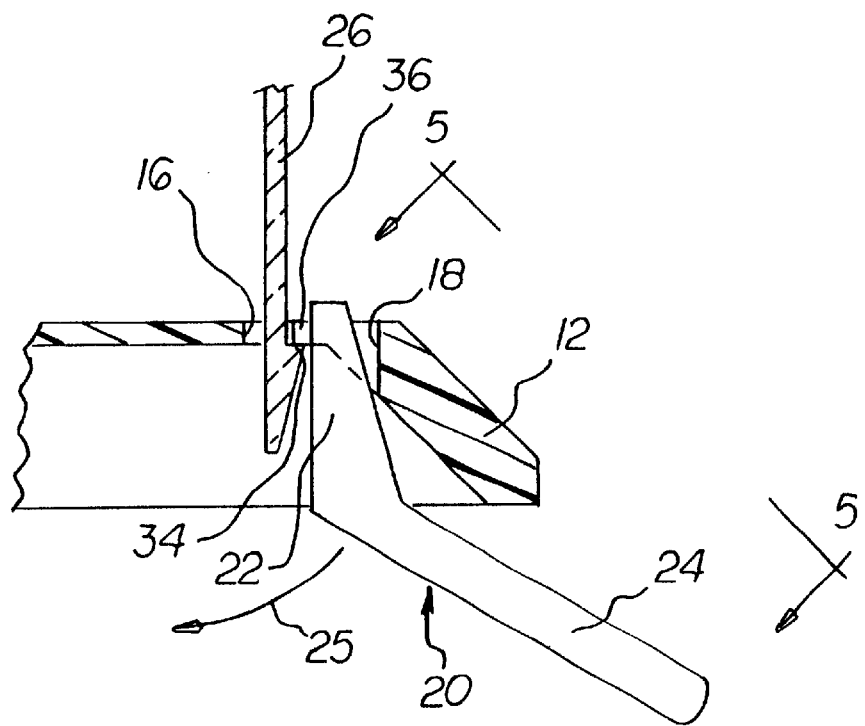
FIG. 4 is an enlarged view of the portion of the embodiment of the invention shown in FIG. 3 contained in circled region 4 thereof.
Figure 5:
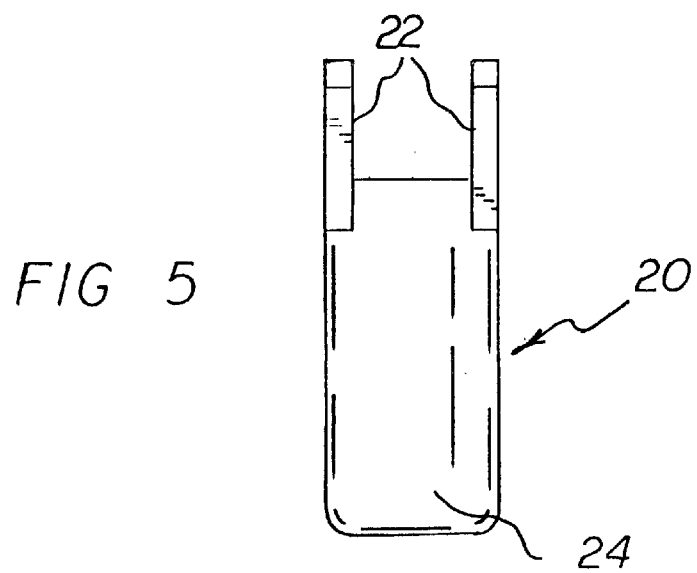
FIG. 5 is an oblique view of the embodiment of the invention shown in FIG. 4 taken along line 5—5 thereof.

However, when it is desired to remove the second limb reception portion 14 from the first limb reception portion 12, a person, such as a healthcare worker, obtains a pair of unlocking keys 20, as shown in FIG. 4. To use the unlocking keys 20, the respective handle ends 24 of the unlocking keys 20 are grasped by a health worker. The unlocking ends 22 of the unlocking keys 20 are inserted into the respective key reception channels 18. Then, the handle ends 24 are pushed downward in the direction shown by arrow 25. As this is done, the front faces of the unlocking ends 22 push against the front sides of the key reception channels 18, and rear faces of the unlocking ends 22 push backward on the front faces of the barbed finger ends 34. As a result, the barbed finger ends 34 are pushed out of engagement with the barb engagement ledges 36, and the second limb reception portion 14 can be pulled upward to allow the barbed finger ends 34 to be pulled upward through the locking finger reception channels 16. In this way, the second limb reception portion 14 can be lifted off of the first limb reception portion 12. Moreover, once the front side of the second limb reception portion 14 is lifted off of the first limb reception portion 12, the second limb reception portion 14 can be rotated further around the hinge pins 42, and the hinge-pin-reception wells 46 can be removed from the hinge pins 42 so that the second limb reception portion 14 can be completely separated from the first limb reception portion 12.

Clearly, without having use of an unlocking key or keys 20, it would be very difficult for a person, especially a child, to separate the second limb reception portion 14 from the first limb reception portion 12 and disturb an I/V needle in one's arm.

The designation "I/V" as used herein and in the appended claims means "intravenous" as is well recognized in the art of medicine.

The components of the patient mounted I/V protector apparatus of the invention can be made from inexpensive and durable metal and plastic materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved patient mounted I/V protector apparatus that is low in cost, relatively simple in design and operation, and which may advantageously be used with young patients to retain an I/V needle in a desired intravenous position. With the invention, a patient mounted I/V protector apparatus is provided which covers the portion of the I/V needle that is outside the patient's arm so as to prevent the patient from touching or disturbing the I/V needle. With the invention, a patient mounted I/V protector apparatus is provided which protects the portion of the I/V line that is adjacent to the I/V needle from being pulled by the patient. With the invention, a patient mounted I/V protector apparatus is provided which blocks a distal pulling force on an I/V line from being transmitted through the I/V line to the I/V needle. With the invention, a patient mounted I/V protector apparatus is provided which can be easily fixed to an removed from a patient's forearm.

With the invention, a patient mounted I/V protector apparatus is provided which can be ornamented with attractive decorations, such as cartoon characters, which are appealing to children. With the invention, a patient mounted I/V protector apparatus is provided which can be written upon to receive personalized messages or signatures of friends and loved ones. With the invention, a patient mounted I/V protector apparatus is provided which precludes a child from disconnecting a top limb reception portion from a bottom limb reception portion. With the invention, a patient mounted I/V protector apparatus is provided which needs a key to disconnect the top limb reception portion from the bottom limb reception portion. With the invention, a patient mounted I/V protector apparatus provides that the top limb reception portion is connected to the bottom limb reception portion, in part, by a hinge or pivoting motion. With the invention, a patient mounted I/V protector apparatus provides a snap lock connection between the top limb reception portion and the bottom limb reception portion.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Hence, the proper scope of the present invention should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed as being new and desired to be protected by Letters Patent of the United States is as follows:

1. A patient mounted I/V protector apparatus, comprising:
    first limb reception portion which is placed under a patient's arm, wherein said first limb reception portion includes locking finger reception channels, an I/V tubing support member projecting upward from said first limb reception portion, and one or more tubing securement members attached to said I/V tubing support member, and
    a second limb reception portion which is connected to said first limb reception portion, wherein said second limb reception portion includes locking fingers which are placed in registration with said locking finger reception channels for locking said second limb reception portion to said first limb reception portion.

2. The apparatus of claim 1 wherein said first limb reception portion includes straps for securing the patient's arm to said first limb reception portion.

3. The apparatus of claim 2 wherein said straps include strap ends, wherein one of said strap ends includes a quantity of a hook-or-loop connector and another of said strap ends includes a quantity of complimentary loop-or-hook connector.

4. The apparatus of claim 1 wherein said locking fingers are flexible.

5. The apparatus of claim 1 wherein:

said locking fingers include barbed finger ends, said locking finger reception channels include barb engagement ledges for engaging said barbed finger ends.

6. The apparatus of claim 5 wherein:

said locking fingers are located on a front side of said second limb reception portion, and said locking finger reception channels and said barb engagement ledges are located on a front side of said first limb reception portion.

7. The apparatus of claim 1 wherein said I/V tubing support member includes a tubing reception channel.

8. The apparatus of claim 1 wherein said second limb reception portion includes ventilation channels.

9. The apparatus of claim 1, further including:

an arm-reception cushion supported on said first limb reception portion.

10. A patient mounted I/V protector apparatus, comprising:

first limb reception portion which is placed under a patient's arm, wherein said first limb reception portion includes locking finger reception channels, a second limb reception portion which is connected to said first limb reception portion, wherein said second limb reception portion includes locking fingers which are placed in registration with said locking finger reception channels for locking said second limb reception portion to said first limb reception portion, guide pins projecting upward from a rear side of said first limb reception portion, and guide slots located on a rear said of said second limb reception portion, wherein said guide slots are registrable with said guide pins.

11. The apparatus of claim 10, further including:

hinge pins supported horizontally on said rear side of said first limb reception portion, and hinge-engagement members supported on said rear side of said second limb reception portion.

12. The apparatus of claim 11 wherein each of said hinge-engagement members includes a hinge-pin-reception well for being placed in registration with and for receiving a hinge pin.

13. A patient mounted I/V protector apparatus, comprising:

first limb reception portion which is placed under a patient's arm, wherein said first limb reception portion includes locking finger reception channels, a second limb reception portion which is connected to said first limb reception portion, wherein said second limb reception portion includes locking fingers which are placed in registration with said locking finger reception channels for locking said second limb reception portion to said first limb reception portion, key reception channels adjacent to said locking finger reception channels in said first limb reception portion, and an unlocking key which includes an unlocking end and a handle end, wherein said unlocking end is received in said key reception channels.

* * * * *